United States Patent [19]

Borggrefe et al.

[11] Patent Number: 4,536,325
[45] Date of Patent: Aug. 20, 1985

[54] PREPARATION OF STABLE OIL-IN-WATER EMULSIONS OF HIGH OIL CONTENT

[75] Inventors: Gerhard Borggrefe, Dusseldorf; Christian Hase, Erkrath; both of Fed. Rep. of Germany

[73] Assignee: Henkel Kommanditgesellschaft auf Aktien, Duesseldorf, Fed. Rep. of Germany

[21] Appl. No.: 573,521

[22] Filed: Jan. 24, 1984

[30] Foreign Application Priority Data

Jan. 31, 1983 [DE] Fed. Rep. of Germany ....... 3303174

[51] Int. Cl.$^3$ ............................................. B01J 13/00
[52] U.S. Cl. .................................... 252/314; 252/312; 71/DIG. 1; 564/106; 514/558; 514/560
[58] Field of Search ................ 252/312, 314; 564/106; 424/172

[56] References Cited

FOREIGN PATENT DOCUMENTS 708428  7/1941  Fed. Rep. of Germany .
1644942 6/1971  Fed. Rep. of Germany .
428091  5/1935  United Kingdom .

*Primary Examiner*—Richard D. Lovering
*Attorney, Agent, or Firm*—Ernest G. Szoke; Nelson Littell, Jr.; Henry E. Millson, Jr.

[57] ABSTRACT

Stable oil-in-water emulsions containing more than 60% by weight of non-aqueous phase may be prepared using water-soluble salts of monoacyl cyanamides, of which the acyl radical contains from 10 to 20 carbon atoms, as emulsifiers. The monoacyl cyanamides of $C_{12}$–$C_{18}$ fatty acids are preferably used in the form of their sodium salts. The oil-in-water emulsions preferably contain from 70 to 95% by weight of non-aqueous phase and from 0.1 to 3% by weight of emulsifier.

2 Claims, No Drawings

4,536,325

PREPARATION OF STABLE OIL-IN-WATER EMULSIONS OF HIGH OIL CONTENT

BACKGROUND OF THE INVENTION

German published application DE-AL No. 16 44 942 describes stable, thixotropic oil-in-water emulsions containing at least 80% by volume and preferably up to 95% by volume of non-aqueous, inner phase. The emulsifiers used for preparing these emulsions consist primarily of alkoxylation products of relatively high molecular weight alcohols, alkoxy phenols, carboxylic acids, amines, amides or polyols.

However, the production of these emulsions is relatively complicated because, at the beginning of emulsion formation, the oil to be emulsified has to be added to the aqueous, emulsifier-containing phase in small portions over a prolonged period. The full effect of the emulsifier required for forming stable emulsions is only developed at an advanced stage of the emulsion forming process. On an industrial scale, a procedure such as this is time-consuming and also expensive to implement and monitor in terms of equipment and personnel.

Accordingly, there was a need to develop an emulsifier system of which the effect is sufficient for complete emulsion formation, even when the total quantity of non-aqueous phase is added all at once to the aqueous, emulsifier-containing phase.

OBJECTS OF THE INVENTION

An object of the present invention is the obtaining of a stable oil-in-water emulsion containing more than 60% by weight of non-aqueous phase, characterized in that the emulsifier consists of at least one water-soluble salt of monoacyl cyanamide containing from 10 to 20 carbon atoms in the acyl.

Another object of the present invention is the development of an improvement in a process for the preparation of stable oil-in-water emulsions containing more than 60% by weight of oily non-aqueous phase consisting of the steps of dissolving an emulsifier in the amount of water desired for the final oil-in-water emulsion, adding the oily non-aqueous phase, mixing, and recovering the stable oil-in-water emulsion, the improvement consisting of employing a water-soluble salt of a monoacyl cyanamide containing from 10 to 20 carbon atoms in the acyl as said emulsifier.

These and other objects of the invention will become more apparent as the description thereof proceeds.

DESCRIPTION OF THE INVENTION

The present invention relates to a stable oil-in-water emulsion containing more than 60% by weight of non-aqueous phase, characterized in that the emulsifier consists of at least one water-soluble salt of monoacyl cyanamide containing from 10 to 20 carbon atoms in the acyl as well as the process of preparing the same.

Monoacyl cyanamides and their salts are known from German patent DE-PS No. 708,428 and British patent GB-PS No. 428,091. They may be obtained by reacting carboxylic acids or derivatives thereof with cyanamide or an alkali metal cyanamide. If monoacyl cyanamides are formed, they are converted into the corresponding neutral salts by neutralization with alkalis or ammonium bases.

The use of the compounds as a soap substitute and as wetting agents and dispersants is mentioned in the patents cited above. There is nothing in the prior art, however, to indicate that the salts of the monoacyl cyanamides are suitable for the production of oil-in-water emulsions having high oil contents in excess of 60% by weight.

The quantity of emulsifier required for the rapid and complete formation of stable emulsions is comparatively small and preferably amounts to between 0.1% and 3% by weight and, more particularly, to between 0.5% and 2% by weight, based on the emulsion. The monoacyl cyanamides are used in the form of their water-soluble salts, for example salts of sodium, potassium, magnesium, ammonium and of ammonium bases, such as mono-, di- or triethanolamine. They are preferably used in the form of their sodium salt.

The acyl radicals may be aliphatic, cycloaliphatic or alkyl aromatic acyl radicals. They are preferably derived from saturated or unsaturated, preferably straight-chain monocarboxyl fatty acids containing from 12 to 18 carbon atoms. Suitable fatty acids or fatty acid mixtures may be obtained from natural fats, such as coconut oil, tallow, palm kernel oil, palm oil, tall oil, cottonseed oils, sunflower oil, rapeseed oil or fish oils.

Acyl cyanamides derived from $C_{12}$–$C_{14}$-fatty acids are particularly suitable for emulsions having very high oil contents, that is oil contents in excess of 90% by weight.

The oil phase may be formed by any non-aqueous, emulsifiable compounds, but primarily by aliphatic, cycloaliphatic, aromatic and alkyl aromatic hydrocarbons, and also by ester-like or ether-like fats and waxes, fatty alcohols and fatty acids and also mixtures thereof.

The non-aqueous phase may make up from 70% to 95% by weight of emulsions such as these. The emulsions are distinguished by high stability in storage, even at elevated temperature, and may be diluted as required with water.

The emulsions may contain additional active ingredients to make them suitable for the particular application envisaged. These additional active ingredients include, for example, pharmacologically and therapeutically active substances, cosmetics, dyes and fragrances, pigments, oxidation inhibitors, biocides, herbicides, corrosion inhibitors or oxidizing agents and, optionally, other emulsion auxiliaries, thickeners and consistency regulators.

In addition the invention relates to an improvement in a process for the preparation of stable oil-in-water emulsions containing more than 60% by weight of oily non-aqueous phase consisting of the steps of dissolving an emulsifier in the amount of water desired for the final oil-in-water emulsion, adding the oily non-aqueous phase, mixing, and recovering the stable oil-in-water emulsion, the improvement consisting of employing a water-soluble salt of a monoacyl cyanamide containing from 10 to 20 carbon atoms in the acyl as said emulsifier.

The production of the emulsions does not require any particular measures and may be carried out, for example, by dissolving the emulsifier in the quantity of water selected, optionally with heating; adding the oil phase and then mixing both phases. Where a high-speed mixer is used, mixing times of 1 to 2 minutes are generally sufficient for forming homogeneous, stable emulsions. Where the emulsifiers according to the invention are used, the oil phase does not have to be incorporated in stages.

Emulsions containing from 70% to 80% by weight of oil phase are generally liquid to viscous while emulsions having a higher oil content are generally paste-like in consistency. Under shear loads, they show thixotropic behavior, i.e. when the load is removed, they soon return to their original viscosity.

The following examples are illustrative of the invention without being limitative in any manner.

EXAMPLES

The following monoacyl cyanamides in the form of their sodium salts were used as emulsifiers in the Examples (CA=abbreviation for cyanamide): $E_1$=lauroyl CA, $E_2$=myristoyl CA, $E_3$=coconut oil fatty acid CA, $E_4$=palmitoyl CA, $E_5$=stearoyl CA, $E_6$=tallow fatty acid CA.

The oily phase consisted of mineral oil (diesel oil), paraffin oil, white spirit, xylene, oleic acid decyl ester and 2-octyl decanol. To prepare the emulsions, the emulsifier was dissolved with heating in distilled water and the particular oil phase subsequently added with stirring. The stirrer was operated at a speed of approximately 16,000 to 17,000 r.p.m. The mixing time (including the time for adding the oil phase) amounted to 2 minutes.

The stability of the emulsions was tested after storage for 3 to 6 weeks at a temperature of 25° C. and after storage for 1 to 3 weeks at a temperature of 40° C. The results are shown in the following Table in which the symbol + indicates that the emulsion in question did not show any signs of separation.

Individual emulsions were stored for 52 weeks at 25° C., after which their viscosity was measured at 25° C. using a Brookfield rotational viscosimeter (spindle speed 6 and 12 r.p.m.).

The results which are also shown in the Table indicate clear thixotropy under the shear effect of the measuring spindle.

TABLE I

| Example | Emulsifier % by weight | Oil phase % by weight | Stability 25° C. 6 W | Stability 40° C. 3 W | Viscosity 6 r.p.m. mPa.s | Viscosity 12 r.p.m. |
|---|---|---|---|---|---|---|
| 1 | 0.5% E1 | mineral oil | + | + | — | — |
| 2 | 1.0% E1 | 75% | + | + | 10600 | 3320 |
| 3 | 1.0% E2 | | + | + | 6200 | 2040 |
| 4 | 0.5% E3 | | + | + | — | — |
| 5 | 1.0% E3 | | + | + | 7200 | 2240 |
| 6 | 1.0% E4 | | + | + | — | — |
| 7 | 1.0% E5 | | + | + | — | — |
| 8 | 1.0% E6 | | + | + | 4200 | 1300 |
| 9 | 1.0% E1 | mineral oil | + | + | — | — |
| 10 | 1.0% E2 | 90% | + | + | — | — |
| 11 | 1.0% E4 | | + | + | — | — |
| 12 | 1.0% E6 | | + | + | — | — |
| 13 | 1.0% E2 | mineral oil | + | + | — | — |
| 14 | 0.5% E1 | 95% | + | + | — | — |
| 15 | 1.0% E1 | paraffin oil | + | + | 4600 | 1580 |
| 16 | 1.0% E2 | 75% | + | + | — | — |
| 17 | 1.0% E3 | | + | + | 10900 | 3200 |
| 18 | 1.0% E6 | | + | + | 2800 | 930 |
| 19 | 1.0% E1 | paraffin oil | + | + | — | — |
| 20 | 1.0% E6 | 90% | + | + | — | — |
| 21 | 1.0% E4 | white spirit | + | + | — | — |
| 22 | 1.0% E5 | 75% | + | + | — | — |
| 23 | 1.0% E1 | white spirit | + | + | — | — |
| 24 | 1.0% E2 | 90% | + | + | — | — |
| 25 | 1.0% E4 | xylene 75% | + | + | — | — |
| 26 | 1.0% E4 | xylene 90% | + | + | — | — |
| 27 | 0.5% E1 | 2-octyl decanol 75% | + | + | — | — |
| 28 | 1.0% E1 | | + | + | 22000 | 5600 |
| 29 | 1.0% E2 | | + | + | — | — |
| 30 | 1.0% E3 | | + | + | 11000 | 3120 |
| 31 | 1.0% E4 | | + | + | 4200 | 1360 |
| 32 | 1.0% E6 | | + | + | 5000 | 1520 |
| 33 | 1.0% E1 | 2-octyl decanol 90% | + | + | — | — |
| 34 | 1.0% E6 | | + | + | — | — |
| 35 | 0.5% E1 | oleic acid decylester 75% | + | + | — | — |
| 36 | 1.0% E1 | | + | + | 4900 | 1480 |
| 37 | 1.0% E2 | | + | + | — | — |
| 38 | 1.0% E3 | | + | + | 13500 | 3800 |
| 39 | 1.0% E4 | | + | + | 11200 | 3280 |
| 40 | 1.0% E5 | | + | + | — | — |
| 41 | 1.0% E6 | | + | + | 9200 | 2700 |
| 42 | 1.0% E2 | oleic acid decylester 90% | + | + | — | — |
| 43 | 1.0% E6 | | + | + | — | — |

The preceding specific embodiments are illustrative of the practice of the invention. It is to be understood, however, that other expedients known to those skilled in the art or disclosed herein may be employed without departing from the spirit of the invention or the scope of the appended claims.

We claim:

1. A process for the preparation of stable oil-in-water emulsion containing from 70% to 95% of oily non-aqueous phase consisting of the steps of dissolving an emulsifier in the amount of water desired, adding the oily non-aqueous phase in one stage, mixing for one to two minutes in a high speed mixer and recovering the stable oil-in-water emulsion, employing from 0.1% to 3% by weight of the emulsion of at least one water-soluble salt of monoacyl cyanamide where said acyl is derived from fatty acids containing from 12 to 18 carbon atoms, as said emulsifier.

2. The process of claim 1 wherein said at least one monoacyl cyanamide is present in the form of its sodium salt.

* * * * *